(12) United States Patent
Stahl et al.

(10) Patent No.: US 8,027,431 B2
(45) Date of Patent: Sep. 27, 2011

(54) SYSTEM AND METHOD FOR DYNAMIC STROBE ARC THERAPY

(75) Inventors: Johannes N. Stahl, Walnut Creek, CA (US); Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/543,437

(22) Filed: Aug. 18, 2009

(65) Prior Publication Data

US 2010/0322381 A1    Dec. 23, 2010

Related U.S. Application Data

(60) Provisional application No. 61/219,662, filed on Jun. 23, 2009.

(51) Int. Cl.
*A61N 5/10* (2006.01)
*A61B 5/05* (2006.01)

(52) U.S. Cl. .......................... 378/65; 600/427

(58) Field of Classification Search ............ 378/64, 378/65, 68, 91, 96, 97, 106, 108, 210; 600/427–429; 250/492.1

See application file for complete search history.

(56) References Cited

U.S. PATENT DOCUMENTS

| | | | | |
|---|---|---|---|---|
| 5,339,347 | A * | 8/1994 | Slatkin et al. | 378/65 |
| 7,027,557 | B2 * | 4/2006 | Llacer | 378/65 |
| 2004/0071261 | A1 * | 4/2004 | Earl et al. | 378/65 |
| 2004/0165696 | A1 * | 8/2004 | Lee | 378/65 |
| 2006/0045238 | A1 * | 3/2006 | Nguyen | 378/65 |
| 2008/0298550 | A1 * | 12/2008 | Otto | 378/65 |
| 2009/0225942 | A1 * | 9/2009 | Shepard et al. | 378/65 |
| 2010/0183120 | A1 * | 7/2010 | Nord et al. | 378/65 |

* cited by examiner

*Primary Examiner* — Anastasia Midkiff (57) ABSTRACT

Some embodiments include receiving a radiation treatment plan for delivering at least a portion of a prescribed radiation dose to a target volume in a series of individual treatment beams, each individual treatment beam defined by a segment including start angle and a stop angle, and delivering a portion of the prescribed radiation dose to the target volume over each of the segments, the segments arranged in a contiguous manner on an arc.

28 Claims, 6 Drawing Sheets

200

```
┌─────────────────────────────────────────────────────────┐
│ RECEIVE A RADIATION TREATMENT PLAN FOR DELIVERING       │
│ AT LEAST A PORTION OF A PRESCRIBED RADIATION DOSE TO A  │
│ TARGET VOLUME IN A SERIES OF INDIVIDUAL TREATMENT BEAMS,│
│ EACH INDIVIDUAL TREATMENT BEAM POSITIONED AT A FIXED POINT│
│                                                     205 │
└─────────────────────────────────────────────────────────┘
                             │
                             ▼
┌─────────────────────────────────────────────────────────┐
│ CONVERT EACH FIXED POINT ASSOCIATED WITH EACH           │
│ OF THE INDIVIDUAL TREATMENT BEAMS TO A SEGMENT          │
│ HAVING A START ANGLE AND A STOP ANGLE                   │
│                                                     210 │
└─────────────────────────────────────────────────────────┘
                             │
                             ▼
┌─────────────────────────────────────────────────────────┐
│ DELIVER A PORTION OF THE PRESCRIBED RADIATION DOSE      │
│ TO THE TARGET VOLUME OVER EACH OF THE SEGMENTS,         │
│ THE SEGMENTS ARRANGED IN A CONTIGUOUS MANNER ON THE     │
│ ARC AND THE DELIVERY OF THE PRESCRIBED RADIATION DOSE   │
│ IS CONTINUOUS THROUGH THE SEGMENTS                      │
│                                                     215 │
└─────────────────────────────────────────────────────────┘
```

```
┌─────────────────────────────────────────────────────────┐
│     RECEIVE A RADIATION TREATMENT PLAN FOR DELIVERING   │
│     AT LEAST A PORTION OF A PRESCRIBED RADIATION DOSE TO A │
│     TARGET VOLUME IN A SERIES OF INDIVIDUAL TREATMENT BEAMS, │
│     EACH INDIVIDUAL TREATMENT BEAM POSITIONED AT A FIXED POINT │
│                                                     205 │
└─────────────────────────────────────────────────────────┘
                            │
                            ▼
┌─────────────────────────────────────────────────────────┐
│        CONVERT EACH FIXED POINT ASSOCIATED WITH EACH    │
│        OF THE INDIVIDUAL TREATMENT BEAMS TO A SEGMENT   │
│           HAVING A START ANGLE AND A STOP ANGLE         │
│                                                     210 │
└─────────────────────────────────────────────────────────┘
                            │
                            ▼
┌─────────────────────────────────────────────────────────┐
│       DELIVER A PORTION OF THE PRESCRIBED RADIATION DOSE │
│         TO THE TARGET VOLUME OVER EACH OF THE SEGMENTS, │
│      THE SEGMENTS ARRANGED IN A CONTIGUOUS MANNER ON THE │
│       ARC AND THE DELIVERY OF THE PRESCRIBED RADIATION DOSE │
│              IS CONTINUOUS THROUGH THE SEGMENTS         │
│                                                     215 │
└─────────────────────────────────────────────────────────┘
```

RECEIVE A RADIATION TREATMENT PLAN FOR DELIVERING
AT LEAST A PORTION OF A PRESCRIBED RADIATION DOSE TO A
TARGET VOLUME IN A SERIES OF INDIVIDUAL TREATMENT BEAMS,
EACH INDIVIDUAL TREATMENT BEAM DEFINED BY A
START ANGLE AND A STOP ANGLE
305

DELIVER A PORTION OF THE PRESCRIBED RADIATION DOSE
TO THE TARGET VOLUME OVER EACH OF THE SEGMENTS,
THE SEGMENTS ARRANGED IN A CONTIGUOUS MANNER ON AN
ARC AND THE DELIVERY OF THE PRESCRIBED RADIATION DOSE
IS CONTINUOUS THROUGH THE SEGMENTS
310

SYSTEM AND METHOD FOR DYNAMIC STROBE ARC THERAPY

CROSS-REFERENCE TO RELATED APPLICATIONS

The present application claims priority to U.S. Provisional Patent Application Ser. No. 61/219,662, filed on Jun. 23, 2009 and entitled "HYBRID ARC IMRT", the contents of which are incorporated herein by reference for all purposes.

BACKGROUND

1. Field

The embodiments described below relate generally to the delivery of radiation therapy to a patient according to a "dynamic strobe" delivery scheme. In some embodiments, the "dynamic strobe" delivery scheme may encompass and/or seamlessly combine with one or more other radiation therapy delivery methods.

2. Description

According to conventional radiation therapy, a beam of radiation is directed toward a tumor located within a patient. The radiation beam delivers a predetermined dose of therapeutic radiation to the tumor according to a treatment plan. The delivered radiation kills cells of the tumor by causing ionizations within the cells. A major concern is limiting the damage to healthy tissue surrounding the tumor.

Figure 1:
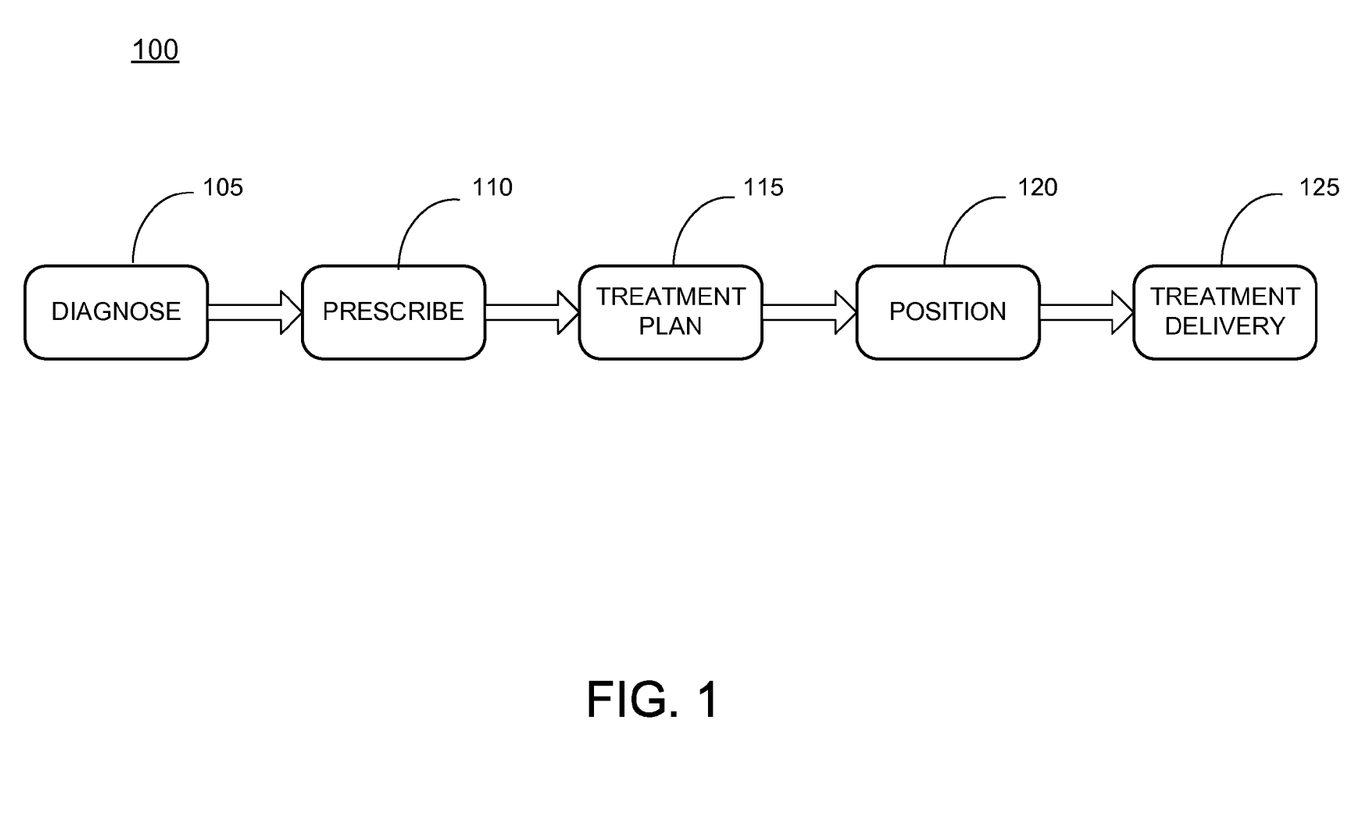
FIG. 1 is a diagram of a radiation therapy process, in accordance with some embodiments herein.

FIG. 1 illustrates a conventional patient treatment process that includes radiation therapy. According to some examples of process 100, image data of a patient is acquired, and a target volume and critical internal structures are identified based on the image data during diagnosis (105). A radiation dose is prescribed (110) for achieving desired results with respect to the target volume while minimizing damage to the critical structures. Next, a treatment plan for delivering the dose is determined (115).

The treatment plan is then delivered (125) to the patient during several sessions, or "fractions", spaced over some period of days. Prior to each fraction, the patient is positioned (120) as required by the treatment plan. Such positioning may involve the use of lasers, skin markers, etc.

Various methods or modes of radiation therapy delivery have been proposed and utilized. In prior systems, each radiation therapy delivery method is typically implemented using specific modes that require a control system optimized for one specific mode of radiation therapy delivery. Some modes of radiation therapy delivery include, for example, CT Guided IMRT (Intensity Modulated Radiation Therapy), Volumetric Modulated Arc Therapy conventional IMRT, and Dynamic Modulated Arc Therapy. In a CT Guided IMRT system, such as a TomoTherapy® system provided TomoTherapy Incorporated, a linear accelerator is mounted in a ring-shaped gantry and moves in a 360 degree rotation around the patient. During delivery the beam is always on and it is partially blocked or unblocked by a binary MLC (multileaf collimator) that rapidly opens and closes the MLC leaves as the gantry rotates. In a Volumetric Modulated Arc Therapy system, such as provided by the RapidArc™ radiotherapy technology from Varian Medical Systems, an L-shaped gantry performs a 360 degree rotation around the patient. The beam is constantly on and the dose rate may be modulated. Also, the MLC leaves are also in constant motion, thus creating different shapes as the gantry rotates. In a conventional IMRT system, beams with modulated intensity are generated at a number of fixed positions or angles around the patient. These beams are then delivered with the gantry stationary at each fixed position. The beam intensity is modulated by either superimposing several shapes at a fixed position ("Step and Shoot IMRT") or by moving MLC leaves across the beam with varying speeds ("Sliding Window IMRT"). In a Dynamic Modulated ARC therapy system the gantry of the delivery system performs a contiguous rotational motion (360 degrees or less per arc). Throughout the rotational motion, the beam remains on at constant dose rate, and the MLC leaves constantly re-form to maintain a shape which is conformal with the shape of the tumor, as viewed from the respective angle.

During the planning stage (115) for the radiation therapy treatment, a decision is made regarding which delivery mode to use. The decision may be based on a number of factors, including for example the patient's diagnosis, delivery system constraints, time issues related to schedules and availability of the patient and/or radiation therapy systems, etc. After the specific mode of delivery is decided, the treatment plan is determined that is adapted to the specifically chosen delivery mode.

Systems have attempted to address various aspects of the foregoing. For example, a delivery mode may be chosen based on the location of a tumor and the surrounding healthy tissue, the capabilities of treatment systems available for treating the patient, etc. However, trade-offs or compromises may be made since a specific radiation therapy treatment mode is chosen and used. More flexible radiation therapy delivery methods are desired.

SUMMARY

To address at least the foregoing, some embodiments provide a system, method, apparatus, and means to receive a radiation treatment plan for delivering at least a portion of a prescribed radiation dose to a target volume in a series of individual treatment beams in an arc around the target volume, each individual treatment beam having a start angle and a stop angle; and deliver a portion of the prescribed radiation dose to the target volume over each of the segments, the segments arranged in a contiguous manner on the arc and the delivery of the prescribed radiation dose is continuous through the segments.

In some embodiments, a shape and/or dose of each of the treatment beams may be optimized by the treatment plan. A number of different methods, algorithms, and techniques may be used during the treatment planning stage to create the treatment plan. In some embodiments, the treatment plan may be created using a Direct Aperture Optimization algorithm.

In some aspects herein, each segment is also defined by a beam shape, a beam dose, and a beam energy. To ensure adherence to a desired treatment plan, the beam dose for each segment is delivered between the start angle and the stop angle. In some embodiments, the beam dose may be distributed between the start angle and the stop angle at a maximum dose rate centered at about a mid-point between the start angle and the stop angle. In some other embodiments, the beam dose may be distributed substantially equally between the start angle and the stop angle.

In some instances herein, the start angle and the stop angle for at least one of the segments may coincide with each other. In these and other instances, the systems and methods of the present disclosure may provide a flexible radiation therapy delivery mode that can accommodate other radiation therapy delivery modes, at least during one segment. Additionally, the segments of the radiation therapy embodiments presented herein may be organized to reduce a time needed to deliver at least a portion of the prescribed radiation dose to the target volume. The segments may be organized to address other issues or concerns in some embodiments.

Embodiments are not limited to those described herein, as those in the art can readily adapt the descriptions to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the embodiments described herein and sets forth the best mode contemplated therefor. Various modifications, however, will remain readily apparent to those in the art.

Figure 2:
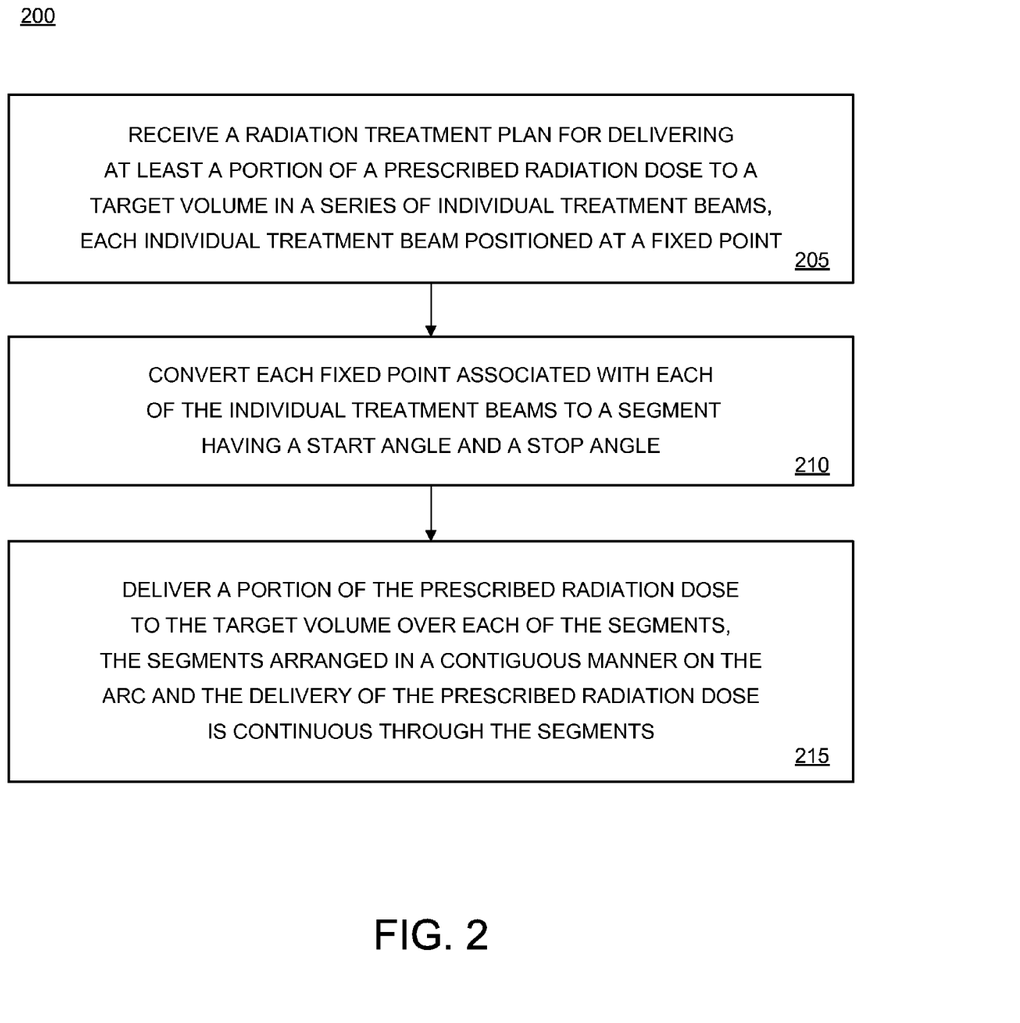
FIG. 2 is a flow diagram of a dynamic strobe modulation ARC therapy process, according to some embodiments.

FIG. 2 is an illustration of a dynamic strobe modulation ARC therapy process 200, according to some embodiments. The illustrated process 200 may be implemented by any suitable hardware and/or software elements. Some embodiments may include hardware elements, some embodiments may include software elements, and other embodiments may include both software and hardware elements in the implementation of the illustrated processes, systems, and devices herein. The process of FIG. 2 is not limited to the order shown therein. Rather, embodiments of the process may be performed in any order that is practicable. For that matter, unless stated otherwise, any methods and processes disclosed herein may be performed in any order that is practicable. Notably, some embodiments may employ one or more portions of the process arranged in different configurations without one or more other portions of the process.

At operation 205, a radiation treatment plan for delivering at least a portion of a prescribed radiation dose to a target volume is received by a radiation therapy system. In some embodiments, the radiation treatment plan is provided to the radiation therapy treatment delivery system embodied in a computer or processor readable medium such as a file or series of files embodied in a memory storage unit. The memory storage unit may be implemented as an optical disk, a CD-ROM, RAM, a flash ROM, or any type of memory storage unit now known or that becomes known in the future.

In some embodiments, the radiation treatment plan received or otherwise provided at operation 205 may be created using the Direct Aperture Optimization (DAO) algorithm. In accordance with the DAO algorithm, the DAO treatment planning algorithm may create a series of individual treatment beams that are placed in a circular configuration around the patient. The location of each beam is specified by a fixed point. The angular position of each beam is called the Optimization Point (OP). The shape and/or dose of each beam is optimized by the DAO algorithm to achieve an optimum dose distribution in the patient based on the planning criteria.

In some embodiments, planning algorithms other than the DAO algorithm may be used to create the treatment plan. For example, a treatment plan created for Conformal Arc Therapy (not based on the DAO algorithm) may be used to create the treatment plan received at operation 205. That is, the treatment planning algorithm, system or methodology used herein may include other treatment planning algorithms in addition to, as a substitute for, a modification of, and an alternative to the DAO algorithm.

As an example, a treatment planning system (not shown) may include a DAO planning system that generates, for example, 36 OP's spaced at 10 degree intervals between each OP around the patient. Again, the shape and the dose of each shape is optimized by the DAO algorithm to achieve an optimum dose distribution in the patient based on the planning criteria.

At operation 210, each OP associated with each of the treatment plan beams is converted to a segment having a start angle and a stop angle. Each segment extends over a range starting with the start angle and terminating with the stop angle. The delivery system herein converts the OP's into segments with defined start and stop angle in order to control the deviation from the original, point-based optimization provided in the treatment plan received at 205. Each segment represents the range over which a prescribed radiation dose associated with an OP is to be delivered, instead of being delivered at the fixed point specified by each OP.

The converting of operation 210 to "spread" the beam dose around the OP between the segment start angle and stop angle may be anticipated by the planning system that generates and provides the treatment plan at 205. The "spreading" of the beam dose may thus be considered and included in the dose calculation to further reduce any small inaccuracies that may result from the converting of operation 210.

Continuing the example introduced above, each of the 36 OP's may be converted into a segment having a defined start angle and a stop angle. Since the treatment plan included 36 OP's, a "final" treatment plan including the segments obtained as a result of converting the OP's to segments includes a sequence of segment for delivering the prescribed radiation dose(s).

At operation 215, a portion of the prescribed radiation dose is delivered over each of the segments. It is noted that the segments are arranged in a contiguous manner in the arc around the patient and the delivery of the prescribed radiation dose is continuous through the segments.

Accordingly, a radiation therapy system configured to deliver radiation therapy in accordance with process 200 may include a gantry that moves in a continuous motion around the patient, and delivers the beams at the OP's without stopping. The dose may be delivered in short strobes (or bursts) of high intensity radiation (e.g., the maximum available dose rate) such that the deviation from the original plan caused by the continuous gantry motion is minimized.

In a traditional step-and-shoot IMRT methodology, the gantry moves from beam to beam, stops at each position, delivers the beam at that position, and then moves to the next fixed position to deliver the next beam, and so on. As compared to the process of FIG. 2, the traditional step-and-shoot IMRT methodology is very time-consuming.

In some embodiments, a 'final' treatment plan in accordance herewith (e.g., obtained at 210) may include a sequence of delivery segments, within which discrete points are described primarily by the parameters of: a beam shape, a beam dose, a beam energy, and gantry angles defining a range or span of the segment (i.e., an upper and lower limit) within which the beam shall be delivered.

Figure 3:
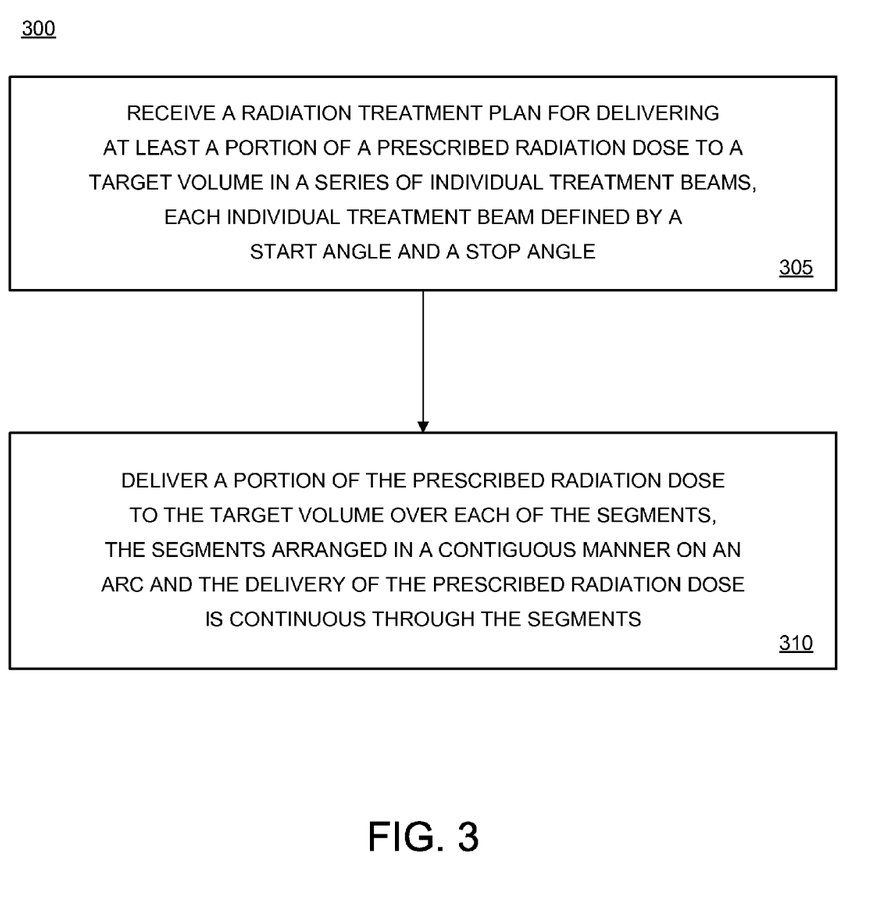
FIG. 3 is a flow diagram of a dynamic strobe modulation ARC therapy process, according to some embodiments.

In some embodiments, a planning system, module, or mechanism may optimize or otherwise provide a segment for delivery of individual treatment beams. FIG. 3 is an illustration of a dynamic strobe modulation ARC therapy process 300, according to some embodiments. The illustrated process 300 may be implemented by any suitable hardware and/or software elements. Some embodiments may include hardware elements, some embodiments may include software elements, and other embodiments may include both software and hardware elements in the implementation of the illustrated processes, systems, and devices herein.

At operation 305, a radiation treatment plan for delivering at least a portion of a prescribed radiation dose to a target volume is received by a radiation therapy system. In some embodiments, the radiation treatment plan is provided to the radiation therapy treatment delivery system embodied in a computer or processor readable medium such as a file or series of files embodied in a memory storage unit. The memory storage unit may be implemented as an optical disk, a CD-ROM, RAM, a flash ROM, or any type of memory storage unit now known or that becomes known in the future.

In some embodiments, the radiation treatment plan received or otherwise provided at operation 305 may provide a series of segments of individual beams defined, at least in part, by a start angle and a stop for each segment. The segments may be optimized by a treatment planning system, module, or mechanism based on the planning criteria using one or more radiation therapy planning algorithms, systems, techniques, and methodologies.

At operation 310, a portion of the prescribed radiation dose is delivered to the target volume over each of the segments as defined by the start and stop angles of the segments. It is noted that the segments are arranged in a contiguous manner in an arc around the patient and the delivery of the prescribed radiation dose is continuous through the segments.

Accordingly, a radiation therapy system configured to deliver radiation therapy in accordance with process 300 may include a gantry that moves in a continuous motion around the patient, delivers the beams at the OP's without stopping, and the dose may be delivered in short strobes (or bursts) of high intensity radiation.

Embodiments of the processes herein will be further described in detail below. Such embodiments will be generally described in conjunction with system 400, a perspective view of which is provided in FIG. 4. Of course, systems other than system 400 particularly depicted in FIG. 4 may be used to implement embodiments described herein.

Figure 4:
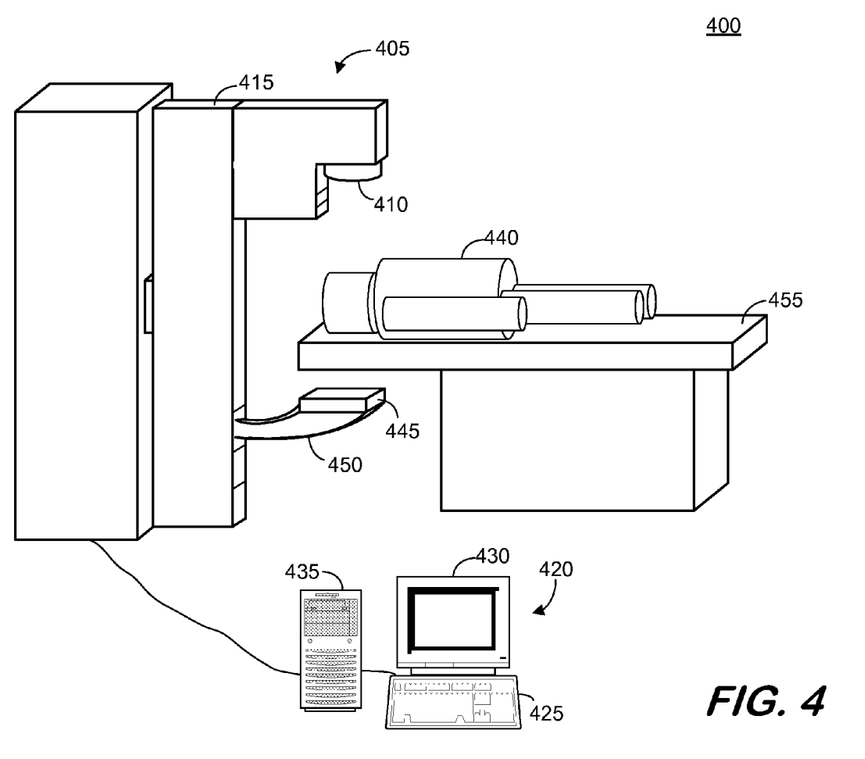
FIG. 4 is a perspective view of a radiation therapy system, according to some embodiments.

System 400 includes linear accelerator 405, operator console 420, patient 440, imaging device 445, and table 455. System 400 may be used to generate radiation for imaging and/or for radiation therapy. In this regard, patient 440 is positioned to receive a radiation dose according to a radiation treatment plan.

Linear accelerator 405 may deliver a radiation beam from treatment head 410 toward a volume of patient 440 that is located at an isocenter of accelerator 405. According to some embodiments, the radiation beam may comprise photon or electron radiation having energies in the megavoltage range. Treatment head 410 includes a beam-emitting device (not shown) for emitting a radiation beam and a beam-shielding device or collimator (not shown) for shaping the beam and for shielding sensitive surfaces from the beam. Treatment head 410 may also include an accessory tray to receive and securely hold attachments used during the course of treatment planning and treatment (such as, for example, reticles, wedges, or the like).

Imaging device 445 may comprise any system to acquire two-dimensional images based on photon radiation (i.e., X-rays) and/or electron radiation received from treatment head 410. Accordingly, imaging device 445 may be suitable for acquiring image data based on megavoltage radiation. Imaging device 445 may be used to acquire images for diagnosis, for verification and recordation of a patient position, for verification and recordation of internal structure positions, and/or for other purposes. In some instances, cone-beam reconstruction techniques may be used to construct three-dimensional images from two-dimensional images acquired by imaging device 445.

In some embodiments, imaging device 445 may be a flat-panel imaging device using a scintillator layer and solid-state amorphous silicon photodiodes deployed in a two-dimensional array. In other embodiments, imaging device 445 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 445 may also comprise a CCD or tube-based camera. Such an imaging device may include a light-proof housing within which are disposed a scintillator, a mirror, and a camera.

Gantry 415 is rotatable around an axis before, during and after emission of the radiation beam. Rotation of gantry 415 may cause treatment head 410 and imaging device 445 to rotate around the isocenter such that the isocenter remains located between treatment head 410 and imaging device 445 during the rotation. Imaging device 445 may be attached to gantry 415 in any manner, including via extendible and retractable housing 450.

Table 455 supports patient 440 during radiation therapy. Table 455 may be adjustable to ensure, along with rotation of gantry 415, that a volume of interest is positioned between treatment head 405 and imaging device 445. Table 455 may be adjusted along any number of axes to accommodate any number of offsets in a position of patient 440.

Operator console 420 includes input device 425 for receiving instructions from an operator and output device 430, which may be a monitor for presenting operational parameters of linear accelerator 405 and/or interfaces for receiving instructions. Such instructions may include a selection from among a plurality of available radiation therapy processes. Output device 430 may also present images acquired by imaging device 445 to verify patient positioning prior to treatment delivery. Input device 425 and output device 430 are coupled to processor 435.

Processor 435 executes program code according to some embodiments. The program code may be executable to control system 400 to operate as described herein. The program code may be stored in storage media of identical or different types, including but not limited to a fixed disk, an optical disk, flash memory, a CD-ROM, a DVD-ROM, a disk, a magnetic tape, and any other storage medium now known or that becomes known.

Operator console 420 may be located apart from linear accelerator 405, such as in a different room, in order to protect its operator from radiation. For example, accelerator 405 may be located in a heavily shielded room, such as a concrete vault, which shields the operator from radiation generated by accelerator 405.

FIG. 4 may include less or more elements than those shown. In addition, embodiments are not limited to the system and devices shown in FIG. 4.

Figure 5:
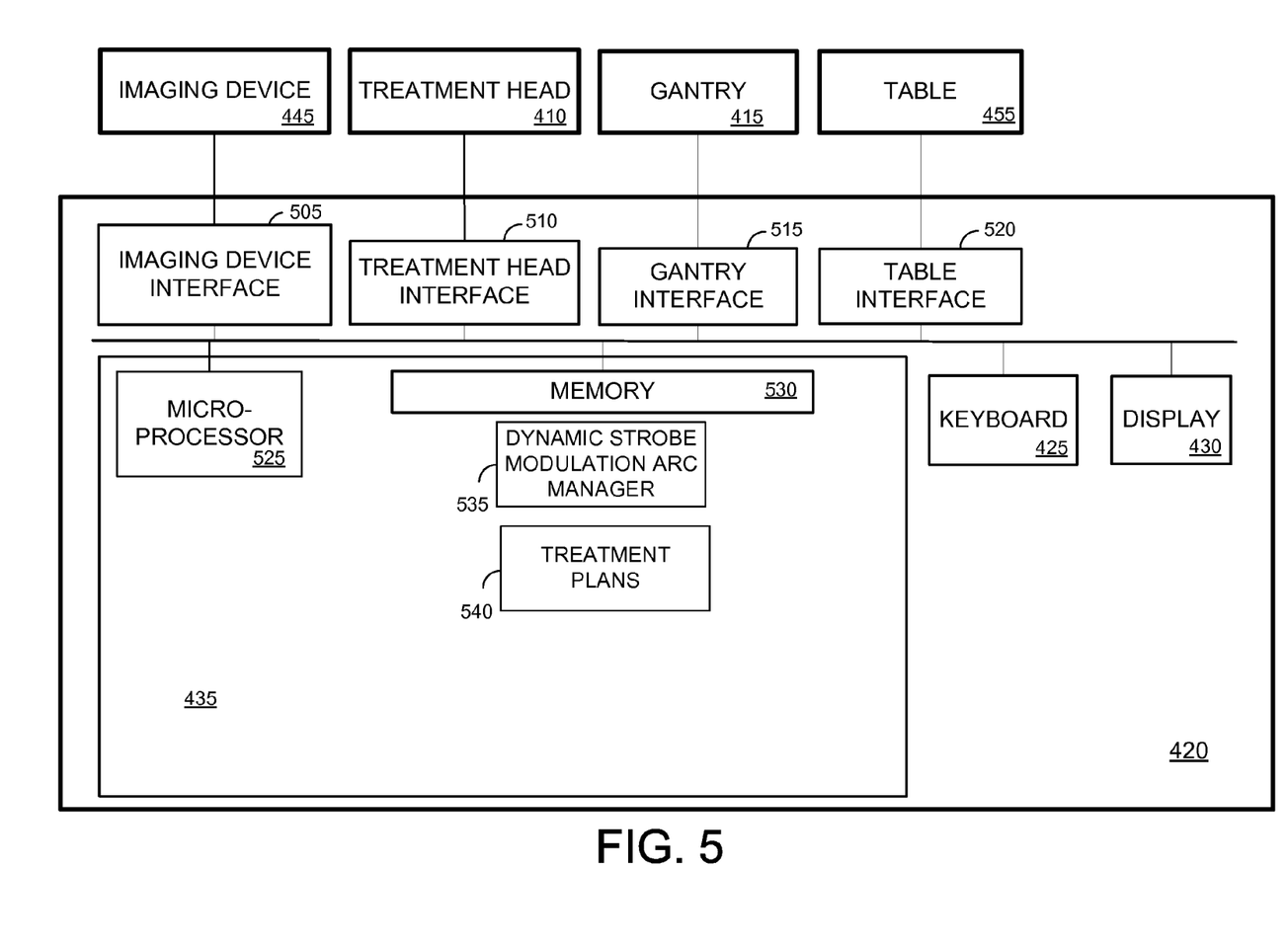
FIG. 5 is a block diagram of a radiation therapy system, according to some embodiments.

FIG. 5 is a block diagram of elements of system 400 according to some embodiments. As shown, operator station 420 includes several elements for interfacing with other elements of system 400. Specifically, operator station 420 includes imaging device interface 505, treatment head interface 510, gantry interface 515, and table interface 520.

Interfaces 505 through 520 may comprise dedicated hardware and/or software interfaces, and one or more of interfaces 505 through 520 may reside in processor 435. One or more of interfaces 505 through 520 may be implemented by a single interface. For example, interface 505 may be implemented by a single Ethernet interface and interfaces 510 through 520 may be implemented by a single proprietary interface for interfacing with table 455, treatment head 410, and gantry 415.

Processor 435 includes microprocessor 525 and memory 530. Microprocessor 525 may execute processor-executable program code stored in memory 530 to provide some or all of the functionality described herein. In this regard, memory 530 stores processor-executable process steps of dynamic strobe modulated ARC therapy manager 535.

Dynamic strobe modulated ARC therapy manager 535 may comprise processor-executable program code to implement process steps 200 and 300. Dynamic strobe modulated ARC therapy manager 535 may also comprise program code to generate and/or modify a treatment plan according to some embodiments.

Memory 530 may also store treatment plans 540 in accordance with any currently- or hereafter-known format. Treatment plans 540 may comprise scripts that are automatically executable by linear accelerator 405 and treatment table 455 to provide radiation therapy fractions. Treatment plans 540 may include one or more treatment plans in which a patient position, a beam plan, and/or a prescribed dose that have been optimized according to some embodiments herein, including but not limited to a DAO algorithm.

Usage of each of modules 535 and 540 will be discussed below, and may comprise any suitable program code to perform the functions attributed thereto. Modules 535 and 540 may comprise any suitable software format, including but not limited to a dynamic link library, a plug-in, an operating system extension, a standalone application, etc. Dynamic strobe modulated ARC therapy manager 535 may comprise module 540 or any other module such as a treatment planning module (not shown), according to some embodiments.

As part of the delivery scheme presented herein, the delivery system of FIGS. 4 and 5 may deliver the beam segments herein, in general, according to the following rules or guidelines.

1. The delivery system will guarantee that each segment is delivered with the correct beam shape, wherein the beam shape will be verified prior to each segment delivery.
2. The delivery system will deliver the prescribed dose while passing between the gantry start angle and the gantry stop angle.
3. The delivery system will distribute the prescribed dose between the start angle and the stop angle in, for example, the following ways:
    (a) The delivery system will deliver the prescribed dose at maximum dose rate, centered about a mid-point between the start angle and the stop angle. This distribution is referred to herein as a "Performance Mode".
    (b) The delivery system will adjust the prescribed dose rate such that the dose is distributed equally between the start angle and the stop angle. This distribution is referred to herein as "Precision Mode".
4. The gantry speed of the delivery system may be adjusted for each beam segment separately such that an overall, aggregate delivery time for all segments is minimized. This may be accomplished by predicting the amount of time required for delivering the entire segment, including beam shaping and all other activities, and adjusting the gantry speed accordingly.
5. If the gantry start angle and the stop angle coincide, the gantry will stop at the prescribed position and will resume movement after the beam has been delivered.

Figure 6:
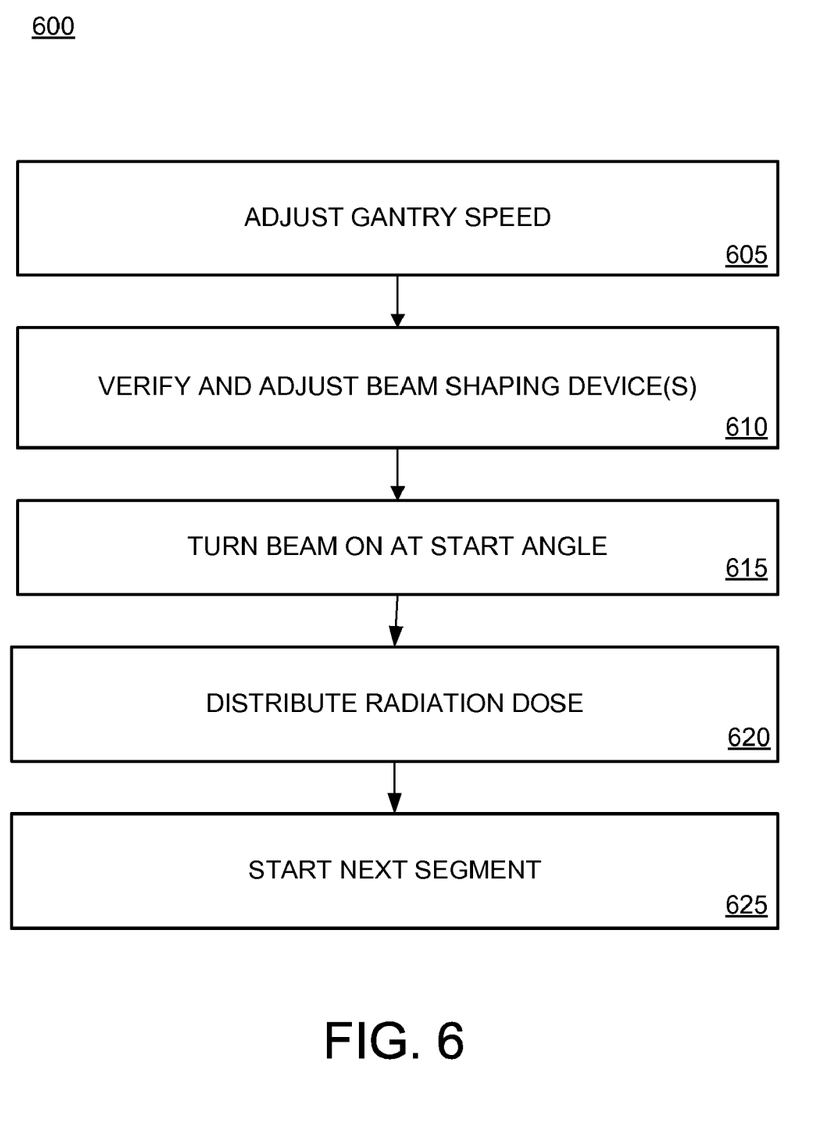
FIG. 6 comprises a flow diagram illustrating a dynamic strobe modulation ARC therapy processes, according to some embodiments herein.

In some embodiments, and in agreement with the general rules or guidelines discussed above, a flow diagram illustrating a dynamic strobe modulation ARC therapy delivery process 600 is depicted in FIG. 6, according to some embodiments herein. FIG. 6 is, in some aspects, a flow diagram of operation 215 of process 200 and of operation 310 of process 300. More specifically, process 600 is intended to represent a delivering of a radiation dose, according to some embodiments. Process 600, as well as all other process steps described herein, may be embodied in whole or in part by hardware of and/or software executed by elements including but not limited to those of system 400. Software (i.e., program code) embodying one or more of the process steps may be stored by any medium, including a fixed disk, flash memory, an optical disk, a CD-ROM, a DVD-ROM, a magnetic tape, or any other storage medium. Some or all of such software may also be stored in one or more devices. The process of FIG. 6 is not limited to the order shown therein. Rather, embodiments of the process may be performed in any order that is practicable. As stated earlier, unless stated otherwise, any methods and processes disclosed herein may be performed in any order that is practicable. Notably, some embodiments may employ one or more portions of the process arranged in different configurations without one or more other portions of the process.

Process 600 may be understood in the context of processes 200 and 300. With regard to process 200, the description will therefore assume that, prior to process 600, operations 205 and 210 have been executed and that a suitable 'final' treatment plan is provided for delivery by the operation 210. With regard to process 300, the description will assumes that a suitable 'final' treatment plan is provided for delivery by the operation 305.

Operation 605 includes adjusting the speed of the gantry (415) of the delivery system (400). In some embodiments, operation 605 may entail adjusting the gantry speed to a pre-calculated value by the delivery system. The speed of the gantry may be calculated by using a prediction of a duration of one segment, more than one segment, or all of the segments in order to minimize a treatment time while also satisfying the start angle and stop angle constraints of the segments. The duration time of the segments may include time for beam shaping, beam delivery, and other factors.

At operation 610, the beam shaping device(s) may be commanded to move to the prescribed shape of the beam. Operation 610, like operation 605, will occur prior to the delivery of a beam during a subject segment. The shape of the beam shaping device(s) may be verified and adjusted in a variety of different manners including, in some embodiments, in real-time as the gantry transitions from one segment to a next segment.

Operation 615 includes a process wherein the beam is turned on and the target volume is irradiated. Operation 615 is initiated when the moving gantry reaches the prescribed start angle. Continuing with process 600 at operation 620, the beam dose is distributed between the start angle and the stop angle. The beam distribution of the dose may be accomplished in a number of different manners, including the Precision Mode and the Performance Mode discussed herein. For example, in Precision Mode the dose rate of the beam will be set such that under constant gantry speed, the end of the dose delivery will coincide with the gantry stop angle. Furthermore, when the prescribed dose has been delivered, the segment ends and the next segment starts, as illustrated at operation 625.

In some embodiments, the beam distribution of the dose may be implemented using a number of different techniques, mechanisms, and methodologies that may vary to deliver the prescribed dose. As such, for example, the speed of the gantry may be dynamically adjusted at or near the start angle, at or near the stop angle, and/or at or near a mid-point (or other multiple points) between the start angle and the stop angle. The speed of the gantry, and other aspects of the delivery system, including but not limited to the size and energy of the treatment beam or the dose rate, may be dynamically adjusted based on different criteria related to a treatment plan and patient. In some embodiments, the rate of the beam distribution of the dose between the start angle and the stop angle may, either alone or in combination with other beam dose distribution optimization aspects, be maximized by using a beam without a flattening filter.

FIG. 6 provides a general flow of beam delivery in accordance with embodiments and aspects herein. However, some embodiments may be configured, adapted, or otherwise have functionality to handle exceptions or special situations that may occur in conjunction with FIG. 6. For example, a radiation delivery system in accordance with embodiments herein may handle the following exceptions:
1. In an instance the beam shaping device does not set to the desired shape by a required time according to the treatment plan, the system will slow down the gantry and eventually stop the gantry (if need be) such that the dose can be delivered within the prescribed start angle and stop angle for the respective segment.
2. In an instance the beam shaping device fails to set the desired shape altogether, the treatment will be interrupted (i.e., aborted).

It is noted that the Dynamic Strobe Modulated ARC Therapy delivery model disclosed herein may encompass other modes of radiation therapy. For example, conventional IMRT may be expressed as a special case of the dynamic strobe delivery wherein the gantry start angle and stop angle of any given segment are equal to each. Accordingly, the prescribed radiation dose will be delivered with a stopped gantry, rather than being delivered with a continuously moving gantry as is the general case in accordance with the Dynamic Strobe Modulated ARC Therapy delivery model disclosed herein.

In some embodiments, hybrid delivery plans may be developed and executed that may include at least one 'standard' IMRT segment, as well as at least one 'dynamic strobe' segments as disclosed herein. The combination or hybrid delivery plans and modes including both 'standard' IMRT (or other modes) segments and at least one 'dynamic strobe' segments in any combination, to meet the treatment objectives. In this manner, a hybrid delivery plan may be developed and administered that includes the advantages of both methods (faster delivery with higher precision where required). For example, a hybrid treatment scheme may provide the accuracy of fixed IMRT in the most critical areas, while preserving the speed advantage of the 'dynamic strobe' ARC delivery wherever accuracy has less impact on the estimated dosimetric calculation.

In some embodiments, the delivery system will organize the segments in such an order and configuration that the delivery can be accomplished in a least amount of time. This aspect of delivery time optimization may be accomplished during a delivery preparation phase. Further, this delivery time optimization may be accomplished by considering a single pass of 360 (or less) degrees of rotation, or multiple passes, as needed. In the instance of a single-pass mode, overlapping segments may be re-ordered and re-sized so that each segment can be delivered within the segment's own start angle and stop angle constraints. The segments may then be re-sorted so that they can be delivered on the expected gantry path.

It is noted that sequence of delivery segments described by a treatment planning system, sub-system, mechanism, or module need not be the same as the sequence of delivery segments re-organized by the intelligence of the delivery system.

In some embodiments, the Dynamic Strobe Modulated ARC Therapy delivery model disclosed herein may include modifying treatment table positions during the beam shaping phase of the beam delivery process to correct for variations in a patient's position.

In some embodiments, the systems and methods herein may support clockwise and counterclockwise delivery, and the direction may be changed dynamically based upon where the gantry position is when the patient is positioned in the delivery system. For each segment, the gantry speed may be calculated such that all the parameters of the treatment plan can be achieved, taking into account the limitations of the system.

Those in the art will appreciate that various adaptations and modifications of the above-described embodiments can be configured without departing from the scope and spirit of the claims. Therefore, it is to be understood that the claims may be practiced other than as specifically described herein.

What is claimed is:
1. A method comprising:
receiving a radiation treatment plan for a prescribed radiation dose to a target volume in a series of individual treatment beams in an arc around the target volume, each individual beam being associated with a fixed point and a prescribed dose of radiation for each fixed point;
converting each fixed point associated with each of the individual treatment beams to a segment having a start angle and a stop angle where the start angle is not equal to the stop angle, each segment defining a range over which the prescribed dose of radiation corresponding to each fixed point is to be delivered, and the segments arranged in a contiguous manner on the arc; and
delivering, by a radiation therapy system including a gantry to control a position of a radiation source, the prescribed dose of radiation from the radiation source to the target volume over each of the segments arranged in the contiguous manner on the arc, the delivery of the prescribed radiation dose is continuous through each of the segments between the start angle and the stop angle of each segment and the gantry of the radiation therapy system moves in a continuous motion about the target volume throughout the delivery of the prescribed dose of radiation to the target volume over each of the segments.
2. The method of claim 1, wherein the fixed points associated with the series of individual treatment beams are spaced apart from each other.

3. The method of claim 1, wherein the treatment plan is created in accordance with a Direct Aperture Optimization algorithm.

4. The method of claim 1, wherein a shape and dose of each of the treatment beams is optimized by a treatment planning system.

5. The method of claim 1, wherein each segment is further defined by a beam shape, a beam dose, and a beam energy.

6. The method of claim 5, wherein the beam shape is verified prior to each segment delivery.

7. The method of claim 5, wherein the beam dose for each segment is delivered between the start angle and the stop angle.

8. The method of claim 7, wherein the beam dose is distributed between the start angle and the stop angle at a maximum dose rate centered at about a mid-point between the start angle and the stop angle.

9. The method of claim 7, wherein the beam dose is distributed substantially equally between the start angle and the stop angle.

10. The method of claim 1, wherein the start angle and the stop angle for at least one of the segments coincide with each other.

11. The method of claim 1, further organizing the segments to reduce a time to provide the delivering of the portion of the prescribed radiation dose.

12. A system comprising:
a memory to store a radiation treatment plan for delivering at least a portion of a prescribed radiation dose to a target volume in a series of individual treatment beams in an arc around the target volume, each individual treatment beam being associated with a fixed point and a prescribed dose of radiation for each fixed point;
converting each fixed point associated with each of the individual treatment beams to a segment having a start angle and a stop angle where the start angle is not equal to the stop angle, each segment defining a range over which the prescribed dose of radiation corresponding to each fixed point is to be delivered, and the segments arranged in a contiguous manner on the arc; and
a radiation therapy system including a gantry to control a position of a radiation source and a processor in communication with the memory, the processor being operable to cause:
delivering, by the radiation therapy system, the prescribed dose of radiation from the radiation source to the target volume over each of the segments arranged in the contiguous manner on the arc and the delivery of the prescribed radiation dose is continuous through each of the segments between the start angle and the stop angle and the gantry of the radiation therapy system moves in a continuous motion about the target volume throughout the delivery of the prescribed dose of radiation to the target volume over each of the segments.

13. The system of claim 11, wherein the fixed points associated with the series of individual treatment beams are spaced apart from each other.

14. The system of claim 12, wherein a shape and dose of each of the treatment beams is optimized by the treatment planning system.

15. The system of claim 12, wherein each segment is further defined by a beam shape, a beam dose, and a beam energy.

16. The system of claim 15, wherein the beam shape is verified prior to each segment delivery.

17. The system of claim 15, wherein the beam dose for each segment is delivered between the start angle and the stop angle.

18. The system of claim 17, wherein the beam dose is distributed between the start angle and the stop angle at a maximum dose rate centered at about a mid-point between the start angle and the stop angle.

19. The system of claim 17, wherein the beam dose is distributed substantially equally between the start angle and the stop angle.

20. The system of claim 12, wherein the start angle and the stop angle for at least one of the segments coincide with each other.

21. The system of claim 12, further organizing the segments to reduce a time to provide the delivering of the portion of the prescribed radiation dose to the target volume.

22. A medium having processor-executable instructions stored thereon, the medium comprising:
instructions for receiving a radiation treatment plan for a prescribed radiation dose to a target volume in a series of individual treatment beams in an arc around the target volume, each individual beam being associated with a fixed point and a prescribed dose of radiation for each fixed point;
instructions for converting each fixed point associated with each of the individual treatment beams a segment having a start angle and a stop angle where the start angle is not equal to the stop angle, each segment defining a range over which the prescribed dose of radiation corresponding to each fixed point is to be delivered, and the segments arranged in a contiguous manner on the arc; and
instructions for delivering, by a radiation therapy system including a gantry to control a position of a radiation source, the prescribed dose of radiation from the radiation source to the target volume over each of the segments arranged in the contiguous manner on the arc and the delivery of the prescribed radiation dose is continuous through each of the segments between the start angle and the stop angle of each segment and the gantry of the radiation therapy system moves in a continuous motion about the target volume throughout the delivery of the prescribed dose of radiation to the target volume over each of the segments.

23. The medium of claim 22, wherein each segment is further defined by a beam shape, a beam dose, and a beam energy.

24. The medium of claim 23, wherein the beam shape is verified prior to each segment delivery.

25. The medium of claim 23, wherein the beam dose for each segment is delivered between the start angle and the stop angle.

26. The medium of claim 25, wherein the beam dose is distributed between the start angle and the stop angle at a maximum dose rate centered at about a mid-point between the start angle and the stop angle.

27. The medium of claim 25, wherein the beam dose is distributed substantially equally between the start angle and the stop angle.

28. The medium of claim 22, further organizing the segments to reduce a time to provide the delivering of the portion of the prescribed radiation dose to the target volume.

* * * * *